United States Patent [19]

Hayashibe et al.

[11] Patent Number: 5,405,582

[45] Date of Patent: Apr. 11, 1995

[54] DEVICE FOR QUANTITATIVELY DETERMINING THE CONCENTRATION OF METALS IN BODY FLUIDS

[76] Inventors: Yutaka Hayashibe; Minoru Takeya; Yasumasa Sayama, all c/o Chuo-kenkyusho, Mitsubishi Materials Corporation, 1-297, Kitabukuro-cho, Omiya-shi, Saitama-ken, Japan

[21] Appl. No.: 268,280

[22] Filed: Jun. 30, 1994

Related U.S. Application Data

[63] Continuation of Ser. No. 81,617, Jun. 23, 1993.

[51] Int. Cl.⁶ ............................................. G01N 21/01
[52] U.S. Cl. ................... 422/68.1; 422/82.05; 422/82.08
[58] Field of Search ............... 422/60.1, 81, 82, 82.01, 422/82.03, 82.05, 101, 82.08; 436/52, 53, 73, 74, 164, 165, 175, 178, 824, 825

[56] References Cited

U.S. PATENT DOCUMENTS

| | | | |
|---|---|---|---|
| 4,491,011 | 1/1985 | Nordmeyer et al. | 73/61.1 |
| 4,819,478 | 4/1989 | Melcher | 73/61.1 C |
| 5,019,515 | 5/1991 | Gisin et al. | 436/52 |
| 5,149,661 | 9/1992 | Gjerde et al. | 436/178 |

*Primary Examiner*—David A. Redding
*Attorney, Agent, or Firm*—Vineet Kohli; Thomas R. Morrison

[57] ABSTRACT

This invention provides a measuring method and a device suitable for the quantitative analysis of metal elements contained in body fluids comprising:

using the flow injection method for reacting a sample with a reagent in a tubule and analyzing the reacted solution. In essence, the present invention provides;

a method for introducing the protein liberated by the reaction of body fluid sample and protein-release reagent into a separating membrane for preventing the passage of protein to separate and remove the liberated protein, and then introducing the reacted solution into a quantitative analysis means for determining and measuring the concentration of target metal contained in the body fluid; and a quantitative analysis device for performing the foregoing method.

7 Claims, 5 Drawing Sheets

DEVICE FOR QUANTITATIVELY DETERMINING THE CONCENTRATION OF METALS IN BODY FLUIDS

This is a continuation of co-pending application Ser. No. 08/081,617 filed on Jun. 23, 1993.

BACKGROUND OF THE INVENTION

This invention relates to a method and a device suitable for the quantitative analysis of metal elements contained in body fluids. The practice of quantitatively analyzing metal elements contained in body fluids has been increasing in importance in the field of clinical medicine, and clinical examinations. For example, zinc exists at 0.9 to 1.1 ppm in the blood serum of healthy men, but it is reported that a lack of zinc causes impairment of the gustatory sense, a decrease in reproductive functions, and growth retardation.

For example, as metal ingredients in the blood are dialyzed during dialysis, adverse reactions such as complications from zinc deficiency tend to develop rather easily. Therefore, determining the level of zinc in blood serum of patients will prove helpful in detecting zinc deficiency, and averting any complications resulting from said deficiency. It is preferable that this quantitative analysis be performed immediately after collection at a medical institute which collects body fluids. In actuality, however, most of the body fluids collected are sent outside for analysis, because the conventional method requires skilled operations, and it takes a long time to get results.

In order to effectively determine the concentration of metal elements in body fluids, it is necessary to remove any proteins from the sample prior to analyzing it. This is necessitated by the fact that proteins generally impede the quantitative analysis of metal elements in body fluids. The protein is liberated by adding a deproteinizing agent such as an acidic solution of trichloroacetic acid, and further separated by centrifugation. Then, after performing a pre-treatment corresponding to a target metal element, the deproteinized sample is introduced into a quantitative analysis device.

As to prior art, please refer to "Conventional Method (Centrifugation and Absorptiometry) for Analysis of Metals in Body Fluids by T. Makino, M. Saito, D. Horiguchi and K. Kina: Clinical Chimica Acta, Vol. 20, 127–135 (1982)".

The following problems are associated with the conventional method, mentioned above:

(1) A large amount of sample of about 0.2 to about 0.5 ml or more is usually required for the analysis.
(2) Since a series of analytical steps from deproteinizing to quantitative measurement are performed by batch system, it takes a considerably long time to obtain the results of analysis.
(3) Since the analytical operation is performed in an open system, the probability of contamination of the body fluid sample during the operation is greatly increased.
(4) A skilled technician is needed because the analytical operation is complicated.
(5) The rate of error in the measurement of the concentration of metals is great.

On the other hand, the so-called "flow injection method" is known as a continuous analysis method. This method requires feeding a reagent solution into a tubule by a non-pulsatory quantitative pump, etc., injecting a sample solution into the reagent, mixing the reagent and the sample with one another in the tubule, and then introducing the reacted solution into a quantitative analysis device. In this method, the required amount of the sample is small; the likelihood of contaminating the sample is almost nil because the steps of mixing, reaction, and dilution are performed in the tubule; and an automatic determination of the concentration of the target metal element can be performed with high precision and within a short period of time. Further, since it is possible to control the dispersion of the sample by adjusting the fluid conditions of the system, this method is suitable for analyzing a large number of samples within a short period of time by appropriately changing the conditions according to circumstances. Additionally, the assembly and maintenance of the device is easy and inexpensive.

As to prior art, refer to "Conventional Method of Flow Injection Analysis by T. Deguchi, R. Takeshita, A. Tanaka and I. Sanemasa: Bunseki Kagaku Vol. 37, 247–252 (1988)".

However, direct quantitative analysis of metal elements contained in body fluids by the flow injection method have not been performed so far. This is because, the centrifugal step for isolating proteins from the sample was thought to be indispensable to this method. Thus this method was not deemed suitable for determining the concentration of metal elements in body fluids.

OBJECTS AND SUMMARY OF THE INVENTION

The present invention aims at solving the problems listed in the previously mentioned sub paragraphs (1) to (5) relating to conventional analysis method.

Further, it is an object of the present invention, to provide a method and a device which permits quantitatively analyzing trace amounts of body fluid samples, in order to determine the concentration of said target metal elements in body fluids as a whole.

It is still, another object of the present invention, to provide a method and a device for quantitative analysis of body fluid samples in order to determine the concentration of target metal elements with high accuracy and in a shorter period of time, by applying the flow injection method.

Briefly, this invention comprises:
(1) dissolving the protein by adding a body fluid sample into a carrier solution containing a protein-release reagent in the tubule of the measuring system, or
(2) liberating the protein by adding a body fluid sample into a carrier solution containing a protein-release reagent, and separating the liberated protein by a separating membrane mounted on the tubular channel.

For the quantitative analysis of metal elements contained in body fluids, this invention applies the flow injection method, which generally requires reacting a body fluid sample with a reagent in a tubule, and analyzing the reacted solution.

In essence, the present invention provides:
a first method for introducing a body fluid sample and a reagent into a carrier solution, reacting both solutions with one another in the tubule to liberate the protein from the body fluid sample, and introducing the reacted solution into a quantitative analysis means for determining and measuring the concentration of metals contained in the body fluid; and a second method for introducing the protein liberated by said reaction of the body fluid sample and the protein-release reagent into a separating membrane for preventing the passage of protein to separate and remove the liberated protein, and then introducing the reacted solution into the quantitative analysis means for determining and measuring the concentration of metals contained in the body fluid.

The above, and other objects, features and advantages of the present invention will become apparent from the following description read in conjunction with the accompanying drawings, in which like reference numerals designate the same elements.

DETAILED DESCRIPTION OF PREFERRED EMBODIMENTS

Figure 1:
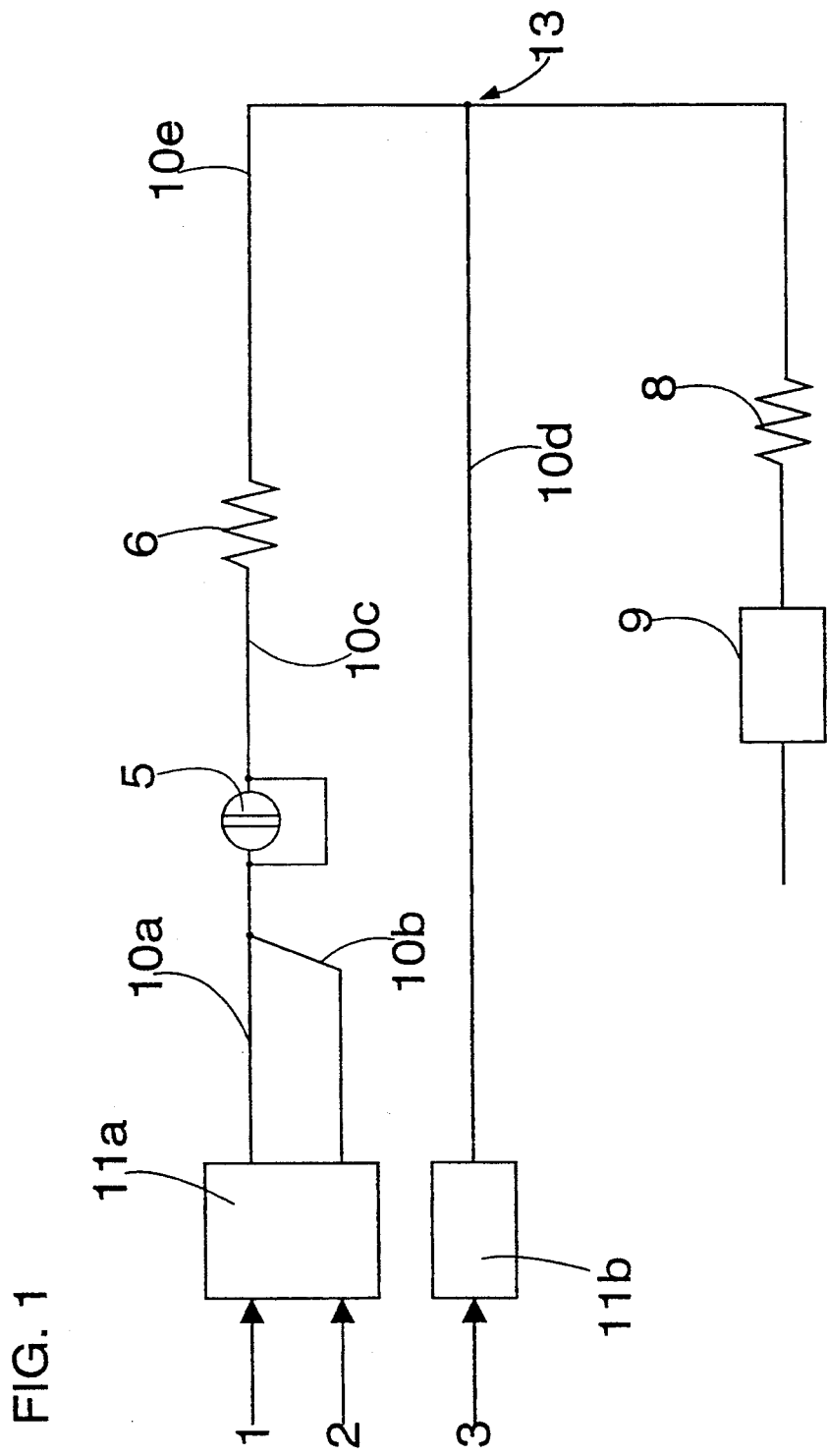
FIG. 1 is a schematic of a quantitative analysis device for the first method of the present invention.
Figure 2:
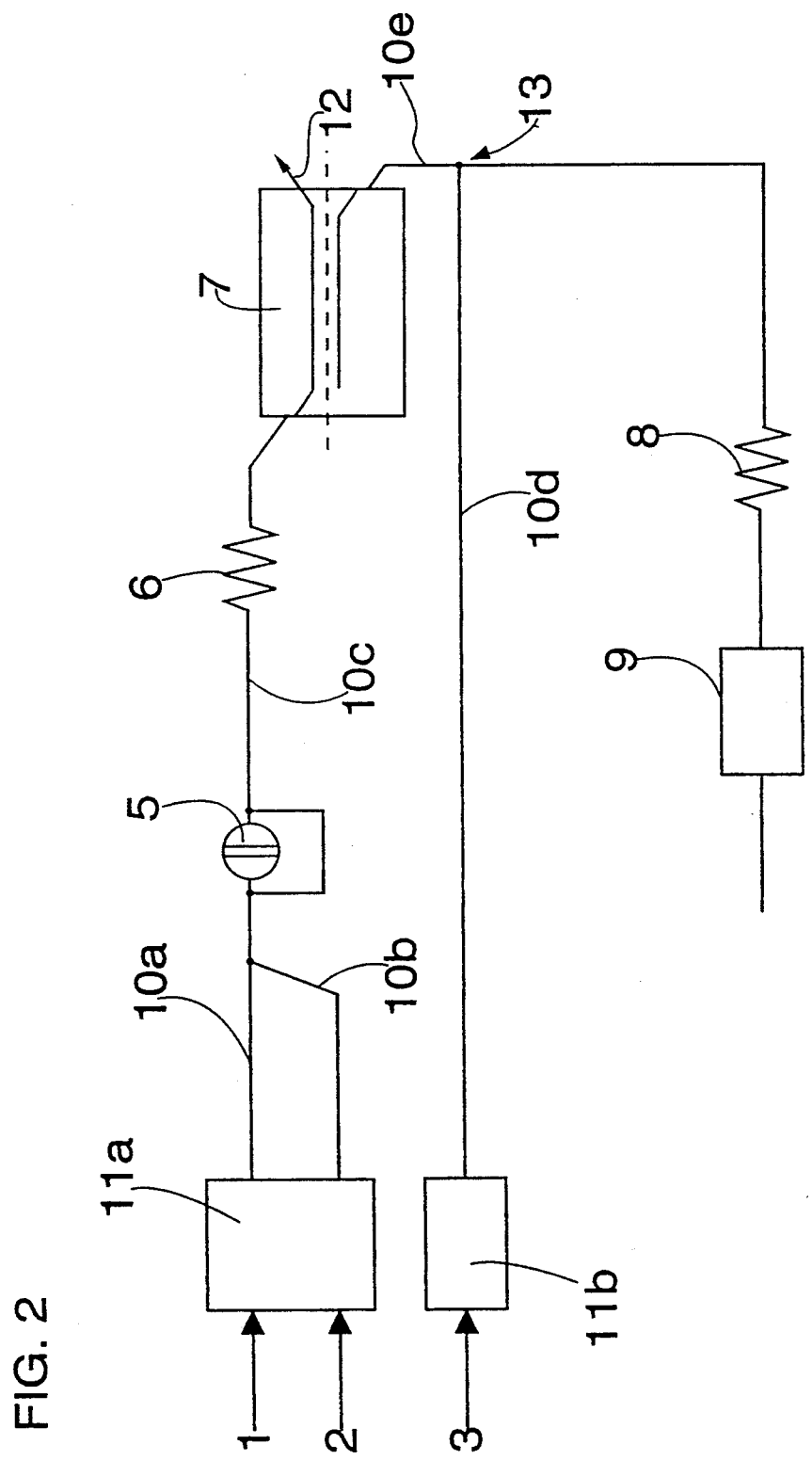
FIG. 2 is a schematic of a quantitative analysis device for the second method of the present invention.

The constitution of the present invention is explained referring to FIGS. 1 and 2. These figures are schematics of quantitative analysis devices invented for performing the first method and second method of the present invention. The same numerals are designated to the device units having the same functions. As shown in these figures, the difference between both devices lies in the presence of the separating membrane part shown by 7 in FIG. 2.

That is, the reacted solution having passed through a reaction part 6, is either (1) introduced as is into a quantitative analysis means 9 to determine and measure the concentration of metals according to the first method, or (2) is introduced into a separating membrane 7, which prevents the protein from passing through it, and thus separates and removes the liberated protein, followed by introducing the reacted solution into a quantitative analysis means 9 to effectively analyze the concentration of metals according to the second method.

Both first and second methods start with introducing a protein-release reagent and a trace amount (usually, 100 μl or so) of body fluid sample into a carrier solution, allowing this mixed solution to flow through a tubule, followed by reacting the protein-release reagent with the body fluid sample in the mixed solution to liberate the protein contained in the body fluid.

In the step involving the introduction of the body fluid sample into the measuring system, the protein-release reagent may be added into the carrier solution containing the body fluid sample, or the body fluid sample may be added into the carrier solution containing the protein-release reagent. However, the latter is simple and convenient in view of the configuration of the device.

The introduced body fluid sample reacts with the protein-release reagent contained in the solution and liberates the protein in the tubule. In this process, it is preferable to meander the tubule in which said reacted solution flows or to form a reaction part wound like a coil in the tubule to secure a sufficient reaction time.

In the case of the first method of the present invention, it is preferable to employ a combination of protein-solubilizing agent and deproteinizing agent as a protein-release reagent. In this event, it is possible to add the deproteinizing agent and then the protein solubilizing agent into the carrier solution, or to add simultaneously the deproteinizing agent and the protein-solubilizing agent. Further, it is also possible to add the deproteinizing agent alone, depending on the kind of target metal for measurement.

Surface active agents which can be used as a protein-solubilizing agent are: dodecyl sodium sulfate, polyvinyl alcohol, acetyltrimethylammonium bromide (CTA-Br), polyoxyethylene (10) octylphenyl ether (product name: Triton-X100), polyoxyethylene glycol sorbitan monoalkyl ester, and the like.

On the other hand, in the case of the second method of the present invention, the protein-solubilizing agent is not necessarily required, but the deproteinizing agent is indispensable, as a protein-release agent.

General deproteinizing agents such as trichloroacetic acid (TCA) and tetramethylammonium hydroxide (TMAH) can be used for both first and second methods.

When TCA is used as a deproteinizing agent, dilute hydrochloric acid, dilute nitric acid, or perchloric acid can be used as a carrier solution. When using TMAH as the deproteinizing agent, dilute sodium chloride solution or water can be used as the carrier solution. The concentration of deproteinizing agent, when used for about 100 μl of body fluid sample, is sufficient to be from about 0.1 to about 0.5 mol/l or so in the reacted solution. Since the rate of dispersion and retention time, characteristic of the flow injection method, is high in the reaction process of said tubule, the body fluid sample is dispersed at a certain rate, and the reaction proceeds at a certain rate in the tubule. Even though the protein from the body fluid sample is not fully isolated and liberated, the amount of protein so liberated over a given period of time remains unchanged. Therefore the step of measuring and determining the concentration of the target metal element should not be adversely affected by the presence of a minuscule amount of unisolated protein.

In the first method, the proteins in the body fluid sample precipitate in an acidic environment such as one with a pH below 6.5. Therefore, when TCA is used, pH of the solution is adjusted to a range of about 6.5 to about 6.9. It is preferred that TMAH be used because it separates and dissolves the protein under a neutral or alkaline condition at pH 7.0 or higher.

For example, when a solution of 0.5M TCA in 0.1M hydrochloric acid (deproteinizing agent) is added to 0.5 ml of human serum sample, the protein is liberated, and the solution becomes turbid. Addition of 0.05M n-dodecyl sodium sulfate (protein-solubilizing agent) to this sample dissolves most of the protein and produces an almost clear solution in which most of the protein dissolves, even though a slight turbidness is observed. Instead of n-dodecyl sodium sulfate, use of polyvinyl alcohol, acetyltrimethylammonium bromide (CTA-Br), polyoxyethylene (10) octylphenyl ether (Triton-X100), or polyoxyethylene glycol sorbitan monoalkyl ester likewise produces a clear solution.

In the second method, the reacted solution is channelled through the separating membrane, which prevents the protein from passing through it. This results in the isolation and liberation of the protein from the body fluid sample and the production of a clear solution. The separating membrane part shown by 7 in FIG. 2, comprises of a separating membrane, which isolates and liberates the protein contained in the body fluid sample by virtue of it having smaller transmitting holes than the molecular diameter of the protein.

This separating membrane fractionates and separates the protein, as the reacted solution passes through it, into an organic phase containing the protein and a liquid phase. Cellulose membranes such as polytetrafluoroethylene membrane (PTFE membrane) with a hole diameter of 0.45 $\mu$m, cellulose acetate membrane with a hole diameter of 0.20 $\mu$m, and cellulose nitrate membrane with a hole diameter of 0.45 $\mu$m, or an aromatic polyamide membrane with a fractional molecular weight of about 20,000, can be employed as a separating membrane. The organic phase containing the separated protein is finally, channelled to the outside of the system.

For example, addition of a solution of 0.5M TCA in 0.1M hydrochloric acid (deproteinizing agent) to 0.5 ml of human serum sample, liberates the protein contained in the sample and produces a white turbid solution. The above solution when passed through a PTFE membrane with a hole diameter of 0.45 $\mu$m, separates into a white turbid organic phase containing the liberated protein and a clear serum. On the other hand, addition of a solution of 10% TMAH by vol in water (deproteinizing agent) to human serum sample produces a slightly yellowish to clear solution from which the protein separates, and the separating of the solution by said PTFE membrane likewise produces a clear serum.

The reacted solution, having passed the process for dissolving the protein by means of a protein-release agent or for removing the protein by the membrane separation of said protein, is then introduced into an analyzing means, which determines and measures the concentration of the target metal elements. As for the analyzing means for determining the concentration of metals in this process, conventional analysis methods for liquid samples can be used, including inductively coupled plasma atomic emission spectrometer (ICP spectrometer), atomic absorption spectrometer, visible/ultraviolet spectrophotometer, infrared spectrophotometer, fluorophotometer, and liquid-phase chromatograph.

In the determining method (the process for determining and measuring the concentration of metals in body fluids), a pre-treatment step may be performed, depending upon the selection of the determining method used to analyze the concentration of metal elements in the body fluid sample.

For example, when using ICP spectrometry or atomic absorption spectrometry as the determining method, the sample solution is diluted by a diluent such as water. When using absorptiometry or fluorophotometry as the determining method, a coloring reagent is added and made to react with the sample solution. If necessary, the pH of the solution should also be adjusted. A buffer as a reagent can also be added depending on the selection of the determining method. If the need arises, plural treatments after deproteinization may also be carried out.

The selection of absorptiometry as the determining method, has the added advantage of ease of operation and convenience. Ordinarily, measuring the concentration of metals in body fluids by absorptiometry, entails adding a coloring reagent corresponding to the target metal to the deproteinized sample solution, allowing for the two to react with each other, and then introducing the reacted sample into the cell of the spectrophotometer, where the absorbance is measured by irradiating a ray of light with a specific wavelength. Then, the absorbance obtained from the standard solution containing the same metal is compared with that from said sample solution to calculate the concentration of the target metal contained in the sample solution. Any one of several conventional coloring reagents can be used in accordance with the kind of a metal to be detected.

Additionally, this measuring method suits automation. As an example, it is possible to convert the absorbance obtained by spectrophotometer into electric signals and send the signals to the operation of a computer to compare with the absorbance of standard solution entered into the computer previously. Thus, the concentration of the target metal in the sample solution is calculated automatically and displayed.

Referring now to the accompanying figures illustrating the measuring device of the present invention, the basic part of this device comprises materials, parts and the like usually used for the flow injection analysis. Tubules with an inside diameter of 1 mm or less are used for the tubular system to permit using a trace amount of sample. The diameter of the tubule may be changed in part, to permit dispersing the body fluid sample in the reacted solution while it flows in the tubular channel. A liquid-feed pump is used to quantitatively feed the solution into the measuring system. Since the pulsation of the solution in the system causes a reduction in the accuracy of measurement and alters the sensitivity of detection, it is preferable to use a non-pulsative pump, such as a double plunger type of pump, as a liquid-feed pump. Tubules themselves, and tubules and other parts forming the tubular channel are connected by connectors to prevent a leakage of liquid, and it is preferable that said connected parts are freely provided or removed.

In the examples of devices illustrated in FIGS. 1 and 2, PTEF tubes with an inside diameter of 0.5 to 1.0 mm are used as tubules 10a to 10e, and a double plunger type of pump is used as a liquid-feed pump 11a to prevent the pulsation of solution. An introduction tubular channel 1 for the protein-release reagent and an introduction tubular channel 2 for the carrier solution are connected to liquid-feed pump 11a.

As the case may be, both introduction tubular channels 1 and 2 may be used as introduction tubular channels for the protein-release reagent, and these tubular channels may introduce the carrier solution in which the deproteinizing agent or the protein-solubilizing agent is dissolved.

Introduction tubular channels 1 and 2 communicate with tubules 10a, 10b, respectively, through liquid-feed pump 11a, join one another after liquid-feed pump 11a, and connect with an introduction part 5 for the body fluid sample. Introduction part 5, for example, has a sample loop with a capacity of 100 $\mu$l, and an automatic valve to open and close said loop. At the time of measurement, the sample loop has already been filled up with the body fluid sample, and a solution of protein-release reagent (if necessary, containing either the deproteinizing agent or protein solubilizing agent or both) is introduced into said sample loop by the automatic valve. The reacted solution containing both protein release reagent and body fluid sample is led to a first reaction part 6. First reaction part 6, as an example, is a PTFE tube wound like a coil with a length of 0.5 m and an inside diameter of 1.0 mm, and while the reacted solution passes first reaction part 6, the proteinrelease reagent reacts with the protein of the body fluid sample to liberate the protein in the tubule.

In the case of the first method of the present invention, the reacted solution passing first reaction part 6 is led into a second reaction part 8 through the tubule, but in the case of the second method, it is led into a membrane separating part 7 through the tubule (as illustrated in FIG. 2). Membrane separating part 7 has a separating membrane with smaller transmitting holes than the molecular diameter of the protein to be liberated, to selectively prevent the passage of said protein across the membrane, and the tubular channel of the measuring system is partitioned by said separating membrane.

As stated above, PTFE membrane with a hole diameter of 0.45 μm, cellulose acetate membrane with a hole diameter of 0.20 μm, cellulose nitrate membrane with a hole diameter of 0.45 μm, or aromatic polyamide membrane with a fractional molecular weight of about 20,000 can also be used as a separating membrane. As the reacted solution passes through the separating membrane part 7, the released protein is prevented from passing through the separating membrane; the liquid phase from which the protein is extracted passes through the separating membrane due to its molecular diameter, leaving behind an organic phase containing the isolated protein. The organic phase is t channelled to the outside of the system by channel 12. While a slight amount of protein (residual protein) remains in the reacted solution after having passed through the separating membrane, it is possible to dissolve this residual protein by adding the protein-solubilizing agent.

The reacted solution, in which the protein has been dissolved or removed, is funneled to a second reaction part 8 through a tubule 10e. A tubular channel 10d for introducing the reagent connects with tubule 10e by a joining part 13. Tubular channel 10d has a liquid-feed pump 11b for feeding the reagent solution, and a tubular channel 3 for introducing a reagent solution connects with liquid-feed pump 11b.

Second reaction part 8, as an example, is a PTFE tube wound like a coil with a length of 0.5 m and an inside diameter of 0.5 mm. While the reagent solution passes second reaction part 8, the reagent reacts with the body fluid sample in the tubule.

When determining the concentration of Zinc in a body fluid sample, for example, 2-(5-bromo-2-pyridylazo)-5-(N-n-propyl-N-(3-sulfopropyl)amino] phenol disodium salt (5-Br-PAPS) is used as a reagent. While the reacted solution passes second reaction part 8, zinc in the body fluid reacts with said reagent to produce a color developing Zn-5-Br-PAPS complex. Second reaction part 8 connects with a spectrophotometer 9. Spectrophotometer 9 may be a commercially available one. The absorbance of sample is measured by spectrometer 9 and compared with that of standard solution to detect the concentration of the target metal.

Preferably, the opening and closing of liquid-feed pumps 11a, 11b, introduction part 5 for body fluids, and individual tubular channels are controlled by computer. Measurement data from the quantitative analyzer 9 is converted into electric signals which are then transmitted to a computer, where the signals are processed automatically.

The devices illustrated in FIGS. 1 and 2 are described above as separate ones, but since both devices are identical to one another, with the exception of separating membrane part 7 shown in FIG. 2, it will be easily understood that the bypassing of tubules before and behind separating membrane part 7, will permit one device to have both functions as shown in FIGS. 1 and 2.

As mentioned above, according to the quantitative analysis method and device of the present invention, only the introduction of a given amount of body fluid sample, together with a reagent, makes it possible to measure the concentration of the target metal. Thus, the analysis operation is very easy and convenient. Furthermore, as the series of steps from the initially introducing the body fluid sample to deproteinizing and isolating the protein by the use of the separating membrane, and finally analyzing the concentration of metal elements, the level of contamination of said sample is greatly reduced, thus yielding highly reliable results. Furthermore, the automation of the aforementioned series of steps, makes it possible to analyze a large number of samples within a short period of time, and produce more reliable results.

EXAMPLES

Embodiment 1

In this embodiment, to explain the first method of the present invention, zinc contained in a human fluid sample was determined by selecting human serum as the body fluid; using TMAH (deproteinizing agent) and Triton X-100 (protein-solubilizing agent) as protein-release reagents; using 5-Br-PAPS as a reagent; and employing a visible spectrophotometer as an analysis means.

In the measuring system comprising the configuration of device illustrated in FIG. 1, a solution of 5% (V/V) TMAH in 0.1M trisodium citrate was introduced from introduction tubular channel 1 at a flow rate of 0.75 ml/min; 1% (V/V) polyoxyethylene (10) octylphenyl ether (Triton X-100) was introduced from introduction tubular channel 2 at a flow rate of 0.75 ml/min; and 100 μl of human serum sample was introduced from introduction part 5 to dissolve the protein in the human serum.

A solution of 0.1% (W/V) salicylaldoxime—1% (V/V) polyoxyethylene (10) octylphenyl ether (Triton X-100)—0.5% (W/V) "5-Br-PAPS"—0.5M ammonium acetate in hydrochloric acid is added as a coloring reagent for zinc into the reacted solution at a flow rate of 1.5 ml/min through introduction tubular channel 3.

When introducing the human serum sample, the concentration of hydrochloric acid in said protein-release reagent solution was adjusted, so that pH of the reacted solution after introduction of the human serum sample was from 8.5 to 9.0.

Absorbance by the Zn-5-Br-PAPS complex formed in the sample solution, after addition of the coloring agent, was measured at a wavelength of 560 nm. The concentration of zinc in the sample solution was measured on the basis of the relation between the concentration of zinc and the absorbance obtained from the standard solution. Ratio-beam spectrophotometer U-1000 of Hitachi, Ltd. having an optical path length of 10 mm was used as a photometer.

Comparison of the results obtained from the present measurement with those from the conventional analysis method is shown in Table 1. In the conventional analysis method, protein was removed by centrifugation, and then the concentration of zinc was determined by atomic absorption spectrometry. Each measurement was performed on six samples, and each sample was measured three times. The mean values is shown in Table 1. The tubular lengths in the first and second reaction parts are 0.5 m in either case.

TABLE 1

| | (unit: ppm) | |
|---|---|---|
| Sample No. | Method of the present invention | Conventional method |
| 1 | 1.4 | 1.1 |
| 2 | 1.2 | 1.2 |
| 3 | 1.1 | 0.7 |
| 4 | 0.8 | 0.7 |
| 5 | 1.1 | 0.8 |
| 6 | 1.4 | 1.1 |

As shown above, the measurement results by the quantitative analysis method of the present invention correspond well with those of the conventional quantitative analysis method. In addition, the accuracy of measurement by the present method is highly reliable, with an error of 5% (C.V. %) when repeating the measurement of the same sample 50 times. The present method permits measuring 20 samples in an hour, and thus a great number of samples can be measured in a short period of time.

Test Example 1

Figure 3:
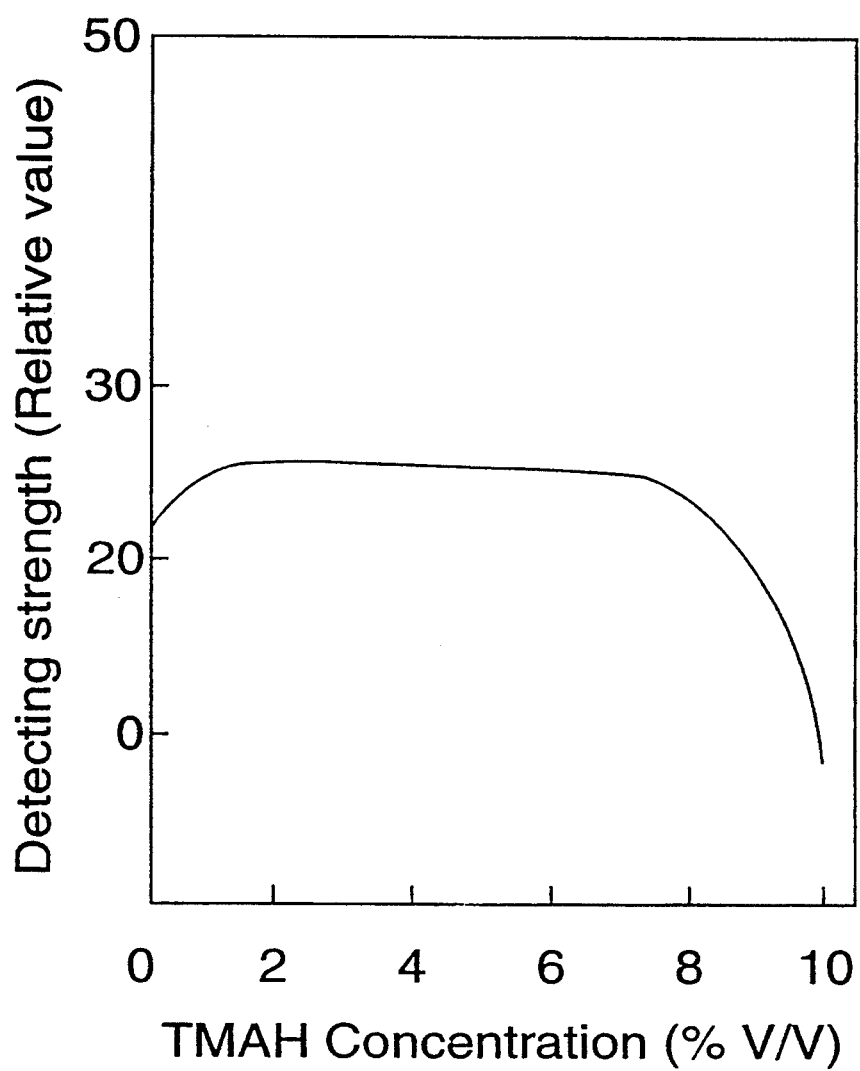
FIGS. 3, 4, and 5 are graphs showing the results of test examples 1 and 2, respectively.

In this quantitative analysis method of the present invention, the influence of the concentration of TMAH as a deproteinizing agent on the measurement was studied. First, in embodiment 1, while the concentration of the other reagent was kept constant, a zinc complex was produced by changing the concentration of TMAH alone between 0 and 10% (V/V), and the absorbance at a wavelength of 560 nm was measured. The results are shown in FIG. 3. As illustrated, almost constant absorbance was detected within the range of 1.0 to 7.5% (V/V) of TMAH concentration. From these results, it has been found that the concentration of TMAH should be adjusted from 1.0 to 7.5% (V/V) to effectively liberate the protein while avoiding the hydrolysis of zinc.

Test Example 2

The influence of the amount of fed liquid and the lengths of first, and second reaction parts on the measurement was studied. The amount of fed liquid was increased, while the ratio of the amounts of liquid in introduction tubular channels 1, 2, and 3 was kept constant. 100 μl of the standard solution containing zinc at concentration of 1.14 ppm was used for the sample solution, and the absorbance at a wavelength of 560 nm was measured. While the tubular channel length of the second reaction part was fixed at 0.5 m, the tubular channel length of the first reaction part was set at 0, 0.5, or 1 m (A: 0 m, B: 0.5 m, and C: 1 m in the figure), and the influence of each length on the measurement was checked. Further, while the tubular channel length of the first reaction part was fixed at 0.5 m, the tubular channel length of the second reaction part was set at 0, 0.5, or 1 m (A: 0 m, B: 0.5 m, and C: 1 m in the figure), and the influence of each length on the measurement was checked.

Figure 4:
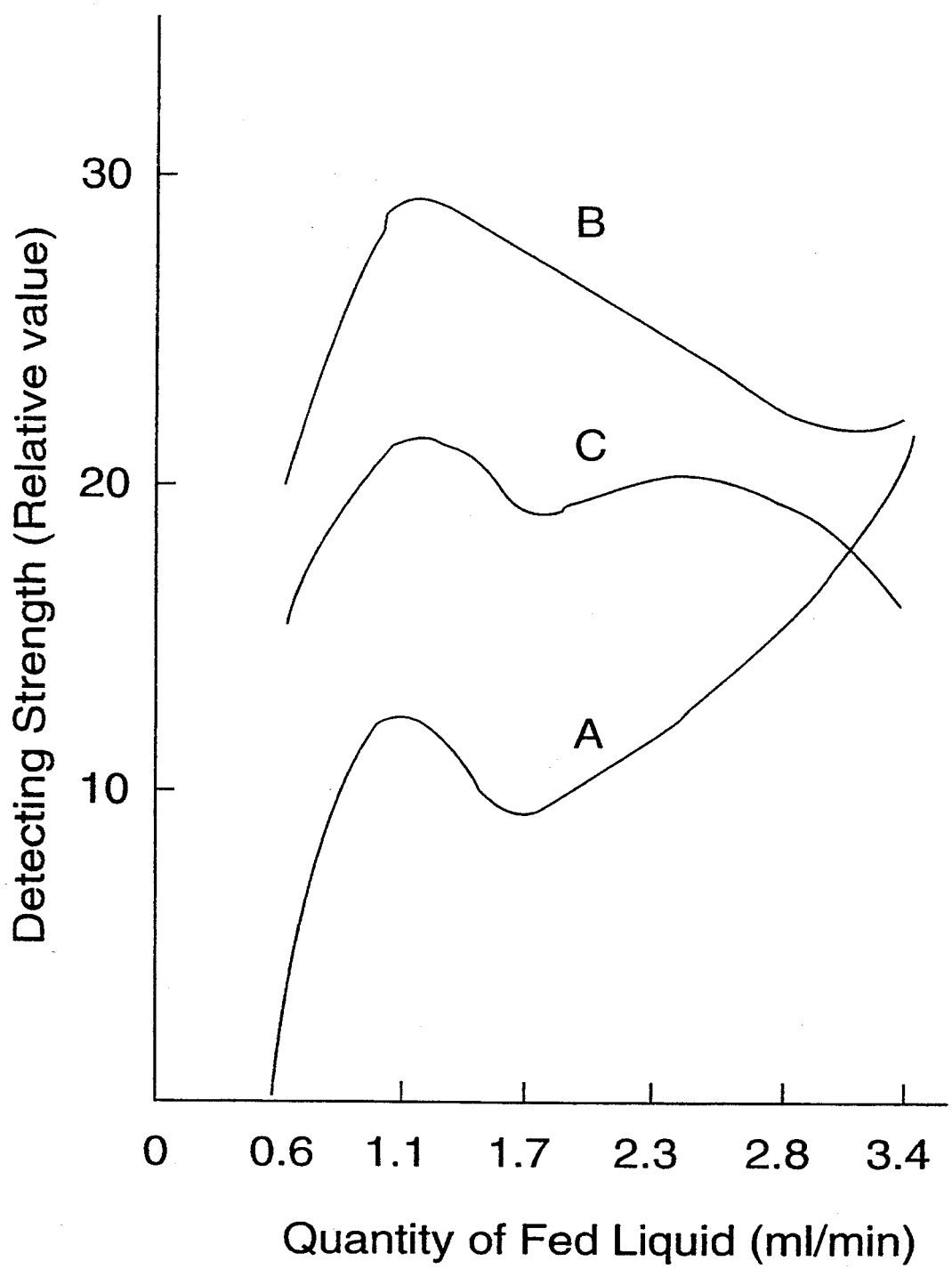
Figure 5:
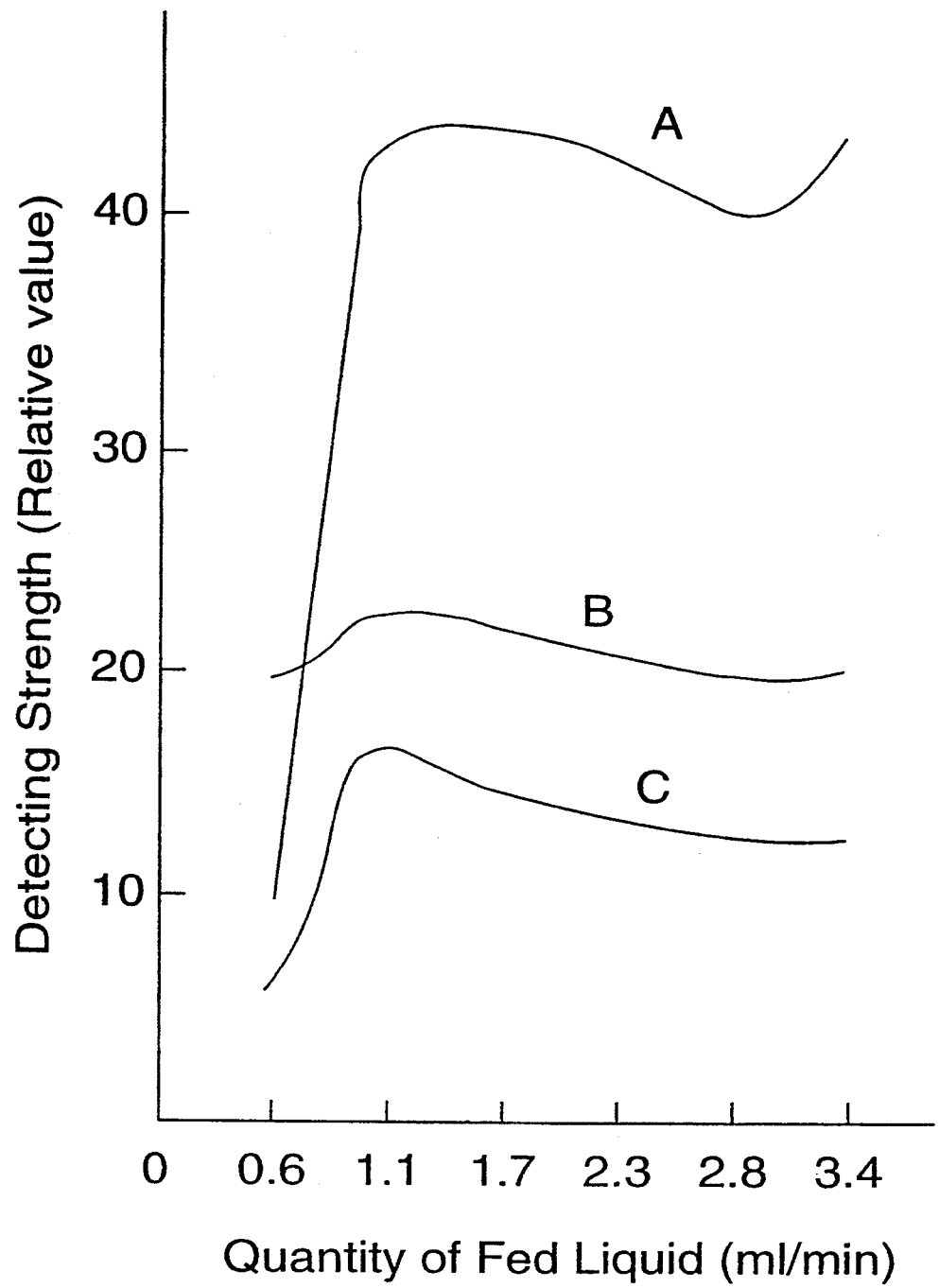

The results of the first reaction part are shown in FIG. 4, and those of the second reaction part are shown in FIG. 5. From the results shown in FIG. 4, it is noted that, when the length of the first reaction part is set at 0.5 m and the amount of fed liquid by pump 11 is set between 1.7 and 3.4 ml/min, the reaction to form a Zn-5-Br-PAPS complex proceeds sufficiently, resulting in the measurement of zinc concentration with the highest sensitivity.

For the second reaction part, even if the intensity of detection in FIG. 5 (A) is high, the accuracy of measurement decreases depending on individual samples. Additionally, if the length of the second reaction part is set at 0.5 m and the amount of liquid fed by pump 11 is set between 1.1 and 3.4 ml/min, the concentration of zinc can be determined with the highest sensitivity.

Test Example 3

In order to coordinate the influence of coexisting elements, known amounts of metal elements and organic substances were added to a human serum sample, and this sample was introduced into the analytical device of embodiment 1 to measure the concentration of zinc. The results are shown in Table 2. Similar to Zinc, it has been found that heavy metals which form complexes with 5-Br-PAPS do not affect the measurement if these heavy metals exist in usual amounts in the human serum. The same results are obtained for organic substances. Iron, however, is thought to affect the measurement and analysis of the metal elements in a body fluid sample, because its concentration probably increases in the sample solution, due to hemolysis at the time of collecting samples.

Therefore, adequate care should be exercises in the collection of such samples.

TABLE 2

| Influence of coexisting substances on body fluid sample | | |
|---|---|---|
| Coexisting substance | Coexistent concentration | Usual concentration in serum solution |
| $Cu^{2+}$ | 3 ppm | 0.8 to 1.3 ppm |
| $Fe^{2+}$ | 5 ppm | 0.8 to 2.0 ppm |
| $Fe^{3+}$ | 5 ppm | 0.8 to 2.0 ppm |
| $Ni^{2+}$ | 0.3 ppm | 0.6 to 5.0 ppb |
| $Co^{3+}$ | 3 ppm | 0.04 to 0.3 ppb |
| $Al^{3+}$ | 3 ppm | 2.0 to 6.0 ppb |
| P | 500 ppm | 115 to 163 ppm |
| $Mg^{2+}$ | 1 mg/ml | 20 ppm |
| $Ca^{2+}$ | 1 mg/ml | 100 ppm |
| Hemoglobin | 1 mg/ml | |
| Bilirubin | 1 mg/ml | |
| Albumin | 50 mg/ml | |
| Trisodium citrate | No interference | |
| Ascorbic acid | No interference | |
| EDTA | No coexistence | |
| Sodium fluoride | 10 mg/ml | |

Embodiment 2

In this embodiment, to explain the second method of the present invention, the concentration of zinc contained in a human fluid sample was determined by selecting human serum as the sample, using TCA (deproteinizing agent) as a protein-release reagent, using 5-Br-PAPS as a coloring reagent, and employing the visible spectrophotometer as an analysis means.

In the measuring system comprising the configuration of the device as shown in FIG. 2, a solution of 0.4M TCA in 0.1M hydrochloric acid was introduced at a flow rate of 0.75 ml/min from introduction tubular channel 1; water or dilute hydrochloric acid as a carrier solution was introduced at a flow rate of 0.75 ml/min from introduction tubular channel 2; 100 μl of human serum sample was introduced from introduction part 5 to liberate the protein contained in the human serum; and the liberated protein was removed by membrane separation.

Successively, as a coloring reagent for zinc, a solution of 0.1% (W/V) salicylaldoxime—1% (V/V) polyoxyethylene (10) octylphenyl ether (Triton X100)—0.5% (W/V) "5Br-PAPS"—0.5M ammonium acetate in hydrochloric acid was added to the sample solution at a flow rate of 1.5 ml/min. In addition, when the human serum sample was introduced, the concentration of hydrochloric acid in said carrier solution was adjusted, so that pH of the reacted solution could be 8.5 to 9.0 after the introduction thereof.

After introduction of the coloring reagent, the concentration of zinc in the sample solution was measured by using the same spectrophotometer and in quite the same way as for embodiment 1.

The comparison of the results of the present measurement and those of the conventional method is shown in Table 3. The conventional analysis method is as described in embodiment 1. The tubular channel lengths of the first and second reaction parts are 0.5 m in either case.

TABLE 3

(unit: ppm)

| Sample No. | Method by the present invention | Conventional method |
| --- | --- | --- |
| 1 | 1.4 | 1.1 |
| 2 | 1.2 | 1.2 |
| 3 | 1.1 | 0.7 |
| 4 | 0.8 | 0.7 |
| 5 | 1.1 | 0.8 |
| 6 | 1.4 | 1.1 |

As shown in the above table, the results of the measurement by the quantitative analysis method of the present invention correspond well with those by the conventional quantitative analysis method. Moreover, when repeating the measurement of the same sample 50 times, the accuracy of measurement was high with an error of 5% (C.V. %) as compared with that of the conventional quantitative analysis method.

According to this analysis method, it is possible to measure 20 samples in an hour, and thus a great number of samples can be measured in a short period of time.

Test Example 4

Influence of the concentration of TCA as a deproteinizing agent, on the measurement of the concentration of metal elements in a body fluid sample, was studied in the same way as for test example 2. First, in embodiment 2, while keeping the concentration of the other reagent constant, only the concentration of TCA was changed between 0 and 1.25M to produce a zinc complex, and the absorbance at a wavelength of 500 nm was measured.

From the results, it has been found that the concentration of trichloroacetic acid should be adjusted to be 0.05M to 1.0M, preferably about 0.4M, to effectively liberate the protein while avoiding the hydrolysis of zinc.

Test Example 5

Influence of the amount of fed liquid as well as the lengths of the first and second reaction parts on the measurement was studied in the same way as for test example 2.

As a result, it has been found that, if the length of the first reaction part is set to be 0.5 m and the amount of fed liquid by pump 11 is set between 1.7 and 3.4 ml/min, the reaction to form a Zn-5Br-PAPS complex proceeds sufficiently, preventing a loss of sensitivity due to the dilution of the sample, and the concentration of zinc can be determined with the highest sensitivity.

Further, it has also been found that, if the length of the second reaction part is set to be 0.5 m and the amount of fed liquid by pump 11 is set between 1.1 and 2.8 ml/min, the concentration of zinc can be determined likewise with the highest sensitivity.

Test Example 6

The same measurement as for test example 3 was performed by employing the analysis device used for embodiment 2, to coordinate the influence of coexisting elements.

The results are quite identical to those of test example 3 shown in Table 2.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A quantitative flow injection analysis device for determining the concentration of metals contained in body fluids comprising:
   (a) a source of a protein-release reagent comprising a protein-precipitating agent;
   (b) a tubular channel in which a carrier solution containing said protein-release reagent flows;
   (c) an introduction part for introducing body fluid sample into said tubular channel;
   (d) a first reaction part of said tubular channel in which the body fluid sample and said protein-release reagent react to form precipitated protein and a liquid phase containing metals;
   (e) a membrane separating part located downstream from said first reaction part for separating, and liberating said protein by preventing the passage of said protein through said separating membrane;
   (f) a second introduction part for introducing a second reagent into said liquid phase having transmitted the separating membrane;
   (g) a second reaction part of said tubular channel in which the metal of said liquid phase reacts with said second reagent to produce a detectable compound; and
   (h) a measuring part for determining the concentration of metal contained in said liquid phase previously introduced from said second reaction.

2. A quantitative analysis device as claimed in claim 1, wherein said measuring part for determining the concentration of metal is at least one device selected from the group consisting of inductively coupled plasma atomic emission spectrometer, atomic absorption spectrometer, visible/ultraviolet spectrophotometer, infrared spectrophotometer, fluorophotometer, and liquid-phase chromatograph.

3. A quantitative analysis device as claimed in claim 1, wherein said measuring part for determining the concentration of metal is a combination of one or more devices selected from the group consisting of inductively coupled plasma atomic emission spectrometer, atomic absorption spectrometer, visible/ultraviolet spectrophotometer, infrared spectrophotometer, fluorophotometer, and liquid-phase chromatograph.

4. A quantitative analysis device as claimed in 1, wherein said separating membrane is at least one membrane selected from the group consisting of polytetrafluoroethylene membrane, cellulose acetate membrane, cellulose nitrate membrane, and aromatic polyamide membrane.

5. A quantitative analysis device as claimed in claim 4, wherein:

said polytetrafluoroethylene membrane having a hole diameter of 0.45 μm;

said cellulose acetate membrane having a hole diameter of 0.20 μm;

said cellulose nitrate membrane, having a hole diameter of 0.45 μm; and;

said aromatic polyamide membrane having a fractional molecular weight of 20,000.

6. A quantitative analysis device as claimed in claim 1, wherein said protein-precipitating agent is at least one of a trichloroacetic acid and tetramethylammonium hydroxide.

7. A quantitative analysis device as claimed in claim 1, wherein said carrier solution is at least one member selected from the group consisting of dilute hydrochloride acid, dilute nitric acid, and perchloric acid.

* * * * *